United States Patent
Adolfsson et al.

(12) 
(10) Patent No.: US 6,843,943 B1
(45) Date of Patent: Jan. 18, 2005

(54) METHOD OF PRODUCING BIOACTIVE COMPOSITE MATERIALS

(75) Inventors: Erik Adolfsson, Uppsala (SE); Leif Hermansson, Uppsala (SE)

(73) Assignee: Doxa Aktiebolag, Uppsala (SE)

( * ) Notice: Subject to any disclaimer, the term of this patent is extended or adjusted under 35 U.S.C. 154(b) by 0 days.

(21) Appl. No.: 09/806,455

(22) PCT Filed: Sep. 29, 1999

(86) PCT No.: PCT/SE99/01729

§ 371 (c)(1),
(2), (4) Date: Mar. 30, 2001

(87) PCT Pub. No.: WO00/19965

PCT Pub. Date: Apr. 13, 2000

(30) Foreign Application Priority Data

Oct. 2, 1998 (SE) ................................. 9803385

(51) Int. Cl.⁷ .......................... A61C 13/00; C04B 33/32
(52) U.S. Cl. .......................... 264/16; 264/604; 264/681; 419/19; 419/49
(58) Field of Search ................................. 264/653, 604, 264/666, 681, 16; 419/10, 19, 49

(56) References Cited

U.S. PATENT DOCUMENTS 4,309,488 A * 1/1982 Heide et al. ................ 428/457
5,096,450 A * 3/1992 Sugimura et al. ............. 419/19
5,306,673 A * 4/1994 Hermansson et al.

FOREIGN PATENT DOCUMENTS

| EP | A2404123 | 12/1997 |
| WO | A1-9011979 | 10/1990 |
| WO | A1-9410100 | 5/1994 |

OTHER PUBLICATIONS

Ceramic Technology and Processing by King, Noyes Publications, 2002.*

* cited by examiner

*Primary Examiner*—Christopher A. Fiorilla
(74) *Attorney, Agent, or Firm*—Birch, Stewart, Kolasch & Birch, LLP

(57) ABSTRACT

The present invention relates to a method of producing improved bioactive composite materials based on apatite, mainly for supporting functions in dental and orthopaedic applications, by adapting closure temperature and applying of pressure in closed systems using the production methods, according to reaction tendencies of the materials at their production, and by possibly further counteracting such reaction tendencies and tendencies for decomposition by additions of helping agents.

2 Claims, 1 Drawing Sheet

METHOD OF PRODUCING BIOACTIVE COMPOSITE MATERIALS

This application is a 371 of PCT/SE99/01729 filed 09/29/1999.

TECHNICAL FIELD

The present invention relates to optimal conditions for producing bioactive materials containing compounds (phases) which have a tendency for decomposition at the production of the material. The invention is specifically relating to materials for use as resistant medical implants.

BACKGROUND OF THE INVENTION

Materials which are used in bioactive contexts often contain phases of differing character. Specifically, any of the included phases may have a large tendency for decomposition at the production, which for metals and especially ceramics take place at an elevated temperature. This commencing thermally activated decomposition may have a directly negative effect on the end product, for example by formation of gaseous compounds which form pores that acts as defects, especially from a strength point of view, or by contributing to the formation of new unwanted phases. A related effect is that decomposition of the phase with a tendency for decomposition is catalysed by the presence of another phase, for example an oxide, which leads to decomposition at temperatures which considerably decrease those for the corresponding pure material with a tendency for decomposition. The presence of an oxide or metal in the bioactive composite material is necessary in order to improve the mechanical properties in relation to pure apatite.

Other related aspects, which however do not concern the basic area of the present application, are e.g. treated, besides in the literature, in the following patents/patent applications: U.S. Pat. No. 3 789 900, DE 330122, U.S. Pat. No. 4 149 893, U.S. Pat. No. 4 957 674, U.S. Pat. No. 4 599 085, DE 29 28 007 Al and JP 62-142 565.

SUMMARY OF THE INVENTION

The present invention relates to composite materials, and a method of producing the same, which material comprises at least one chemically less stable phase, and relates specifically to resistant ceramic implant materials.

The object of the invention is to provide bioactive materials, especially implant materials, with a supporting function in dental or orthopaedic applications with optimal properties, by use of production methods where special consideration has been taken to the bioactive, but chemically less stable, phases included. Key aspects of the invention concern reactions between non active and active (biofunctional) phase, and how these unwanted reactions may be minimised or eliminated or controlled. A new theoretical model has been developed on the decomposition in composite materials, which corresponds to the obtained results according to the present invention.

According to the invention there is thus presented a material and a method of producing the same, in accordance with the enclosed patent claims.

The composite material according to the invention comprises apatite in contents below 90 vol-%, preferably 5–80 vol-%, even more preferred 10–50 vol-% and most preferred 25–45 vol-%. The apatite phase may be pure hydroxyapatite or mixtures of apatite phases, i.e. hydroxyapatite and fluorapatite. The bioinert base mass in the composite material is preferably a construction ceramic, preferably one or more oxides, e.g. aluminium oxide, zirconium oxide and/or titanium oxide. The content of construction ceramic may be 10–95 vol-%, preferably 40–95 vol-% and more preferably 55–85 vol-% and is suitably dominant in the material. As an alternative, the bioinert base mass may be a construction metal in the same concentrations, preferably a Fe or Co—Cr based or Ti, Ta or Zr based construction metal. Low contents (preferably below 10 vol-%) of other phases may also exist besides apatite and bioinert base mass.

DETAILED DESCRIPTION OF THE INVENTION

Figure 1:
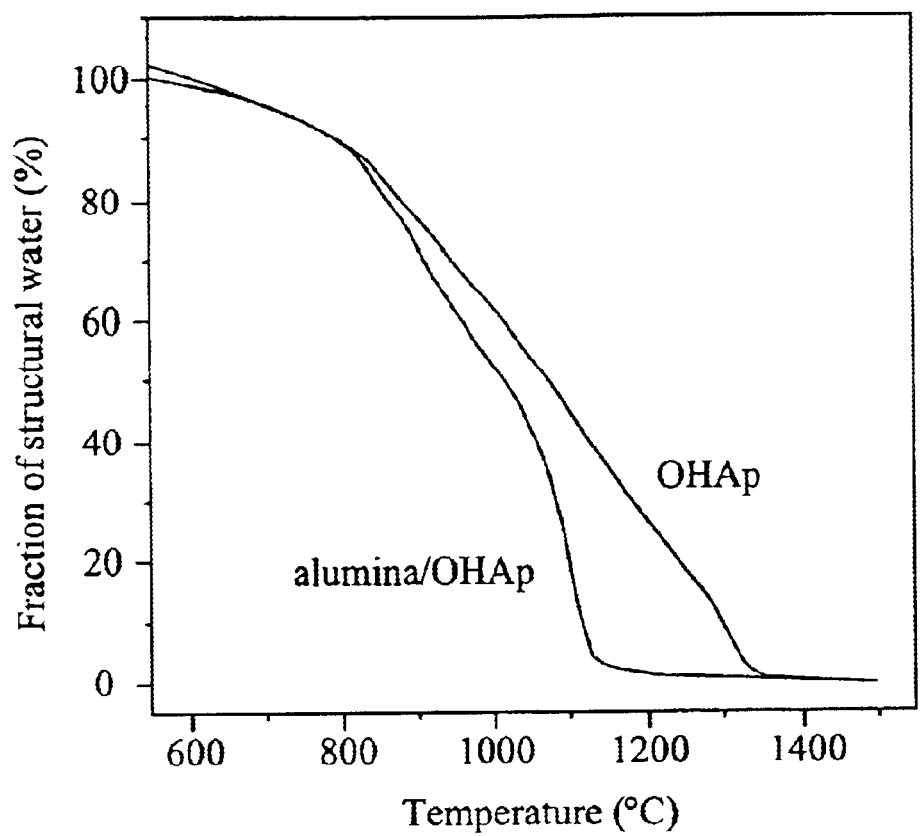
FIG. 1 is a plot of structural water percentages at various temperatures.

It has surprisingly been discovered, in connection with the invention, that the reaction mechanism for decomposition of apatite in the oxide-hydroxyapatite system does not take place according to what is conventionally presented in the literature, but takes place in two steps, where OH groups in hydoxyapatite, $OHAp=Ca_{10}(PO_4)_6(OH)_2$, first leaves the structure, leaving vacancies in the same. When the number of vacancies exceeds a certain critical level, defect OHAp may continue to react with surrounding compounds (e.g. $Al_2O_3$) which catalyse the decomposition. The two steps of the reaction are $$Ca_5(PO_4)_3(OH)_1 \rightarrow Ca_5(PO_4)_3(OH)_{(1-y)}O_{y/2}+y/2\ H_2O \qquad (1)$$

$$2\ Ca_5(PO_4)_3(OH)_{(1-y)}O_{y/2}+Al_2O_3 \rightarrow 3\ Ca_3(PO_4)_2+CaAl_2O_4+(1-y)\ H_2O \qquad (2)$$

This type of decomposition takes place at densification/sintering of the material. By changing the equilibrium reactions decomposition may however be avoided, which may be done in three principally different ways, namely by decreasing the temperature in a closed system, increasing the pressure and/or deliberately introducing the compounds which the active compound strives to decompose to. This leads to that a low sintering temperature should be used, that closing must take place early, before the actual sintering process begins, and that an outer mechanical pressure should be applied to the capsule before the densification begins, at the densification/calcination/sintering of material according to the invention. Furthermore, the initially applied pressure, i.e. the pressure which is applied before the densification begins, should be maintained as a minimum pressure level during the continued densification, i.e. the pressure should normally not be allowed to decrease below the initial pressure during the continued densification/sintering, but should instead be gradually increased.

In the method according to the invention, the powder mixture of apatite and oxide or metal is suitably initially shaped to a raw press body by for example cold isostatic pressing (CIP) or other forming method. Thereafter, the raw press body is densified/sintered, suitable methods being hot isostatic pressing (HIP) or sintering in a closed chamber with possibilities for gas overpressure, overpressure sintering (GPS, gas pressure sintering). At hot isostatic pressing, the raw press body is placed in a pre-shaped capsule, whereafter the capsule is closed. The surrounding gas applies a pressure on the capsule which transmits the pressure to the raw press body itself, which is densified. At overpressure sintering on the contrary, the raw press body is in direct contact with the gas. In both sintering techniques, some type of barrier layer or powder bed may be used, which surrounds the raw press body. To these help layers there may, according to the invention, advantageously be added compounds, e.g. hydrates, which decompose and form compounds which counteract either the decomposition of apatite, or compounds which prevent the metal in the case of metal-apatite composition from being chemically attacked.

According to the invention, closure of the system/capsule and applying of pressure should be performed before commencing substantial decomposition of apatite phase, i.e. at temperatures which are considerably lower than the end temperature for the sintering. In some cases the applying of pressure may be performed already at room temperature, and should generally be performed at temperatures below 900° C., for ceramic based composites preferably below 800° C., even more preferred below 700° C., and for metal based composites preferably below 500° C. This initial applying of pressure may be complete or partial, i.e. the level of the applied pressure may be equal to the end pressure or may be less than the end pressure. The end pressure for HIP is usually very high, most often over 100 MPa, up to 200 MPa or even higher. At sintering in a closed chamber the gas pressure is usually 100–200 atm at the most, i.e. 10–20 MPa. An initial pressure may be 10 MPa or below, down to about 0.2 MPa. At lower temperatures the purpose of such a low initial pressure is primarily to prevent the capsule material from expanding from increased pressure due to the temperature enhancement (according to the perfect gas law) or by deliberately added compounds begin to decompose to gaseous compounds, preferably steam. An initial part pressure at any level between 0.2 MPa and the end pressure is however also conceivable. Exactly which pressure is used is chosen depending on the type of composite system, the type of powder (grain size and morphology), the amount being processed, deliberately added extra decomposing compounds and the type of capsule and sintering technique. The end temperature is, for oxide based materials, typically at least 900° C., usually at least 1000° C. and most often at least 1100° C. For metal based materials, the end temperature is lower, typically about 500–800° C., usually 600–800° C. The end pressure and end temperature is usually maintained for about 1–2 hours.

According to one aspect of the invention the applying of pressure and the temperature enhancement is performed stepwise. The purpose is to apply an increased pressure stepwise, as is needed in connection with the temperature enhancement. A first initial pressure, which is applied already at room temperature and which may be kept at a level of e.g. 0.2–5 MPa, may thereby have the purpose of stabilising the capsule. When the temperature thereafter is additionally increased, the pressure in the capsule increases in accordance with the perfect gas law. At temperature levels below the temperature level for commencing decomposition of apatite phase there is also a commencing decomposition of possibly additionally added helping agents in the form of decomposing compounds (see also below), which also leads to an increase of the pressure in the capsule. Altogether there is therefore required an increased pressure level, of e.g. about 1–10 MPa, as a counter pressure. Finally, when temperature levels are reached where the material of the raw press body itself, the apatite phase, may begin to decompose (see previously mentioned temperature levels) the desired end pressure is applied in order to prevent such decomposition. The temperature is then increased to the desired end temperature and is maintained for the sintering. Exactly how the stepwise pressure application is performed depends on the type of composite system, the type of powder (grain size and morphology), the amount being processed, deliberately added extra decomposing compounds and the type of capsule and sintering technique.

The use of hot isostatic pressing (HIP) in connection with the production of ceramics is of course generally known per se, and has been described also for the oxid-apatite system namely in Swedish patent 465 571. In those contexts there is however not described the capsuling performance itself—closing and early applying of pressure or addition of helping agents in the barrier layer—but only the temperature and pressure at the densification itself. In order to be able to safeguard against decomposition and unwanted reactions at the sintering, the step which precedes the actual hot isostatic pressing (the densification) must also be considered, and be performed according to the present invention, where the temperature at the closing and the temperature at the applying of pressure on the capsule, (or gas pressure in the case of GPS) in the temperature interval before the actual sintering, is adapted to the tendency of decomposition of the existing phases. The use of isostatic compression only as a part of the process for porous apatite, as in WO-A1-9410100, is not working for formation of dense and resistant apatites, and especially not for highly resistant biocomposites of apatite, where decomposition takes place at considerably lower temperatures than for pure apatite, since the decomposition is being catalysed by oxides. See results in example 1. The applying of pressure must take place depending on the tendency of decomposition for different oxide-apatite systems at temperatures below the ones given in WO-A1-9410100.

According to another aspect of the invention, there may be deliberately added an additional decomposing compound in the closed system, which generates a compound that the composite system (mainly the apatite phase) tends to decompose into. Decomposition of the composite material is thereby additionally counteracted. In an especial embodiment there is accordingly also used, besides an early closure and an early stepwise applying of pressure, addition of a decomposing help compound in powder form, which early forms the phases or any phase which the functional phase strives to decompose into in the actual component, whereby the decomposition reaction is driven to a decreased decomposition. In the case of a composite material containing metal and a functional phase (apatite), there may be added a second helping agent which decreases the metal reactions—mainly oxidation. In these cases where densification generally takes place at a lower temperature than for ceramics it is often the metal which is the more reactive phase. In these cases the helping agent is advantageously fine-grained metal powders, e.g. fine-grained iron powder or fine-grained titanium powder, which reduces the oxygen content in the gas environment surrounding the composite material. Help compounds against decomposition of the active phase and helping agents for the preservation of the metal phase may advantageously be added to a barrier layer or powder bed which may surround the component at the processing. In order to prevent decomposition of apatite phases, different types of hydrates which easily give off hydroxyl groups and forms steam and other groups (carbonate, phosphate etc.) may be incorporated as helping agents in a barrier layer or powder bed. Material which is used as a helping agent in this way may generally be a hydrate (for example hydrated cement or salt with crystal water) which gives off water at temperatures which are lower than the temperatures at which decomposition reactions in the oxide-apatite system commences, i.e. at temperatures of at least below 900° C., preferably below 800°

C. and even more preferred below 600° C. The concentration of helping agent, when such is used, is generally low and is adapted for the system in question and the amount of material which is to be processed. In a powder bed the concentration of helping agent is typically less or equal to 10 vol-%, in a barrier layer less than ca 5 vol-%.

The invention is additionally described by a number of embodiment examples.

EXAMPLE 1

FIG. 1 shows an example of how the departure of water takes place from pure hydroxyapatite (OHAp) and from hydroxyapatite in a composite (aluminium oxide with 60 vol-% hydroxyapatite).

The reason for the difference in water departure is decomposition, which for the composite takes place in sequential steps according to reaction 1 and 2 (see the describing text above), and which for pure hydroxyapatite only takes place according to reaction 1. The departure of hydroxyl groups is accelerated by the presence of oxide. The graphs have been plotted by thermogravimetric analysis in a TG apparatus of the brand Seta-ram TAG24. The departure of water is standardized according to the same content of hydroxyapatite.

EXAMPLE 2

Tetragonal stabilised zirkonium oxide powder (TZ) including 45 vol-% hydroxyapatite powder, HA, was hot isostatic pressed with differing closure and applying of pressure but with the same end parameters, namely 1200° C. and 200 MPa for 1 h. In the first case (TZ-HA I), the capsule material of glass was closed at 900–950° C., and the full pressure was applied at 1150° C. In the second case (TZ–HA II), the closing took place at room temperature and with an overpressure of about 5 atm up to 650° C., where 80 atm was applied. At 800° C. there was applied a pressure of 160 MPa which after temperature rise to the top temperature gave the end pressure 190 MPa. An analysis of the micro structure with a scanning electron microscope shows that TZ–HA I contains a number of very small pores and that a part of the tetragonal phase has transferred into a cubic phase at the same time as HA has decomposed into TCP, $Ca_3(PO_4)_2$. The pores have, with high probability, derived from departed OH groups. For TZ–HA II there is obtained a completely dense material with a maintained tetragonal structure, which is beneficial for strength and resistance to rupture. As a comment, decomposition of HA to TCP—which deliberates CaO and which contributes in the phase transformation of tetragonal phase into cubic phase—is hard to detect in a more coarse micro structure, since the decomposition reactions take place in the border line between TZ and HA, the amount reacting depending on micro structure (distribution of TZ grains and HA grains and the size of the grains).

EXAMPLE 3

Titanium dioxide and hydroxyapatite (HA) was mixed and was blended in the grinding in a ball mill with Sialon mill bodies and iso-propanol for solvent, during 4 days. The solvent was driven off in an oven in a closed hood at 90° C. and was finally dried at 450° C. during 2 h. The content of HA was 30 vol-%. Samples were hot isostatic pressed with differing closure and applying of pressure. In test A closure took place at room temperature and a pressure of 3 atm overpressure was applied, which was maintained up to 700° C., where the end pressure of 160 MPa was applied and the temperature was raised to 900° C. and was maintained constant for 1 h. In test B closure and final applying of pressure, 160 MPa, took place directly at 900° C. and was maintained for 1 h. Samples from test A contains the desired phases rutile and HA, while the result from test B shows a certain decomposition and formation of titanate, $CaTiO_3$, together with TCP, $Ca_3(PO_4)_2$. No porosity worth mentioning has been detected. Here too, the possibility of detection through phase analysis with X-ray diffraction depends on HA and micro structure. The tendency of titanate formation is however obvious. Generally, decomposition of HA is hard to detect when the content of HA is less than about 20 vol-% in the composite.

EXAMPLE 4

Aluminium oxide was mixed with hydroxyapatite, HA, according to the method described in Example 2. The content of HA was 45 vol-%. Samples were densified either with hot pressing (HP) at 1200° C., 25 MPa during 2 h, or by hot isostatic pressing (HIP) with full applying of pressure, 160 MPa at 700° C., and a temperature rise to 1200° C., maintained for 2 h. In the hot pressed samples there is shown decomposition of HA to TCP, $Ca_3(PO_4)_2$, while the hot isostatic pressed samples are showing the correct phases containing aluminium oxide and HA.

EXAMPLE 5

A fine-grained steel powder, 316L, is mixed with 40 vol-% hydroxyapatite, HA according to example 2, with the difference that the driving off of solvent takes place at vacuum at 200° C. The material, a cold isostatic pressed body, is placed in a capsule intended for hot isostatic pressing, which is closed under vacuum. An end pressure of 160 MPa is applied at 600° C. during 1 h. Analysis of micro structure (SEM) and phase analysis (X-ray diffraction) show that a completely dense material with maintained HA phase is present in the end product. In the barrier layer of boron nitride there had been added an additional fine-grained metal powder consisting of 316 L in a concentration of 10 vol-%, which was finely powdered by being blended in the grinding during 2 days.

What is claimed is:

1. A method of producing a bioactive composite material, comprising apatite, for dental or orthopedic use, which material comprises groups with a tendency for decomposition, where a densification of the material is performed at high temperatures under pressure, characterized in that the densification is performed in a closed system where applying of a pressure partially or completely takes place before an end temperature for the densification is reached, and before commencing substantial decomposition of apatite phase, characterized in that one or more helping agents are added to a barrier layer at densification by hot isostatic pressing or to a powder bed at densification by over pressure sintering, in order to further suppress unwanted reactions.

2. The method of claim 1, characterized in that said helping agent is a fine-grained metal powder and/or a hydrate.

* * * * *